(12) United States Patent
Koves

(10) Patent No.: US 6,399,843 B1
(45) Date of Patent: Jun. 4, 2002

(54) UPFLOW OLIGOMERIZATION REACTION PROCESS

(75) Inventor: William J. Koves, Hoffman Estates, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/689,526

(22) Filed: Oct. 12, 2000

(51) Int. Cl.⁷ .............................. C07C 2/04; C07C 2/24
(52) U.S. Cl. .................. 585/510; 585/514; 585/515; 585/520; 585/526; 585/527; 585/529
(58) Field of Search ................. 585/510, 514, 585/515, 520, 526, 527, 529

(56) References Cited

U.S. PATENT DOCUMENTS

| | | | |
|---|---|---|---|
| 2,526,966 A | 10/1950 | Oberfell et al. | 196/1 |
| 3,050,472 A | 8/1962 | Morrell | 252/435 |
| 3,050,473 A | 8/1962 | Morrell | 252/435 |
| 3,132,109 A | 5/1964 | Morrell | 252/435 |
| 3,560,167 A | 2/1971 | Bruckner et al. | 23/288 |
| 3,906,053 A | 9/1975 | Lanier | 260/683.15 D |
| 3,916,019 A | 10/1975 | Closson et al. | 260/683.15 E |
| 3,932,553 A | 1/1976 | Robert | 260/683.15 B |
| 3,959,400 A | 5/1976 | Lucki | 260/683.15 R |
| 3,981,940 A | 9/1976 | Zuech | 260/683 D |
| 3,981,941 A | 9/1976 | Butter | 260/683.15 R |
| 3,997,621 A | 12/1976 | Brennan | 260/683.15 B |
| 4,051,191 A | 9/1977 | Ward | 260/671 R |
| 4,255,352 A | 3/1981 | Drake et al. | 260/465.8 R |
| 4,304,948 A | 12/1981 | Vora et al. | 585/315 |
| 4,324,941 A | 4/1982 | Ghirga et al. | 585/466 |
| 4,343,957 A | 8/1982 | Sartorio et al. | 585/449 |
| 4,384,157 A | 5/1983 | DeGraff | 585/514 |
| 4,393,259 A | 7/1983 | Ward et al. | 585/315 |
| 4,695,665 A | 9/1987 | Degraff | 585/450 |
| 4,749,820 A | 6/1988 | Kuo et al. | 585/330 |
| 4,801,432 A | 1/1989 | Galiasso et al. | 422/143 |
| 5,049,360 A | 9/1991 | Harandi et al. | 422/141 |
| 5,789,640 A | 8/1998 | Jin et al. | 585/467 |
| 5,895,830 A | * 4/1999 | Stine et al. | 585/259 |
| 5,990,367 A | 11/1999 | Stine et al. | 585/514 |
| 6,013,845 A | 1/2000 | Allan et al. | 568/728 |

OTHER PUBLICATIONS

*Petroleum Processing Principles and Applications* by R. J. Hengstebeck, McGraw–Hill Book Company, 1959, pp. 208–218.

"Gas Conversion Processes", *Petroleum Refiner*, vol. 31, No. 9, Sep. 1952, pp. 156–157 and 164–165.

"Propylene Polymerization in Packed Reactor, Liquid Phosphoric Acid Catalyst" by S. R. Bethea et al, *Industrial and Engineering Chemistry*, vol. 48, No. 3, Mar. 1956, pp. 370–377.

* cited by examiner

*Primary Examiner*—Thuan D. Dang
(74) *Attorney, Agent, or Firm*—John J. Tolomei; James C. Paschall

(57) ABSTRACT

An oligomerization process for the production of higher aliphatic olefins is disclosed. In the process, a liquid oligomerization feed stream comprising lighter aliphatic olefins is passed to a reactor vessel. The liquid oligomerization feed stream is transported upwardly in the reactor vessel against gravity through a fixed bed of solid oligomerization catalyst under oligomerization conditions. The catalyst has a Hammett acidity value of −4 or less. A liquid saturate stream comprising paraffins is passed into contact with the feed stream and the catalyst. A liquid oligomerization effluent stream is recovered comprising the paraffins and product higher aliphatic olefins.

19 Claims, 9 Drawing Sheets

Axisymmetric Simulation Configuration of Downflow Reactor with Constant Heat Release Axisymmetric Simulation Configuration of Upflow Reactor with Constant Heat Release Axisymmetric Simulation Configuration of Downflow Reactor with Reaction Kinetics Axisymmetric Simulation Configuration of
Upflow Reactor with Reaction Kinetics i-butylene Radial Distribution
axial location: 0.3 m from catalyst bed outlet

UPFLOW OLIGOMERIZATION REACTION PROCESS

FIELD OF THE INVENTION

This invention relates generally to the production of higher aliphatic, olefins from the oligomerization of lighter aliphatic olefins.

BACKGROUND OF THE INVENTION

Prior Art

Processes for the oligomerization of lighter olefins to produce $C_6$ and higher carbon number olefins are well known. Oligomerization processes can be used to produce plasticizer components from propylene. Additionally, oligomerization processes have been long employed to produce good quality motor fuel from butylene. Such oligomerization processes are also referred to as catalytic condensation and polymerization with the resulting motor fuel often referred to as polymer gasoline. Methods have always been sought to improve the octane number of the gasoline boiling range oligomerization products. In addition, the oligomerization process is also susceptible to catalyst fouling from the condensation of heavy oligomers into coke that covers the catalyst.

Another process that has met the continuing demand for the conversion of light hydrocarbons into high octane motor fuels was the alkylation of isobutane with propylene, butenes and amylenes using a hydrofluoric acid (HF) catalyst, commonly referred to as HF alkylation. The HF process has provided a highly successful method for the production of high octane motor fuels.

A number of arrangements are known for using oligomerization in combination with other processes such as saturation and dehydrogenation as substitutes for acid catalyzed isomerization alkylation. Patents disclosing the dehydrogenation of light paraffin stream with oligomerization of the dehydrogenation effluent include, U.S. Pat. No. 4,393,259, U.S. Pat. No. 5,049,360, U.S. Pat. No. 4,749,820, U.S. Pat. No. 4,304,948 and U.S. Pat. No. 2,526,966.

In the oligomerization method of the indirect alkylation process set forth in, for example, U.S. Pat. No. 5,990,367, lighter aliphatic olefins such as $C_3$ or $C_4$ are contacted with a solid phosphoric acid catalyst in the presence of a higher paraffin diluent such as cyclohexane or octane. The presence of the paraffin diluent is believed to promote the oligomerization in the liquid phase to yield predominantly dimerized butylene or trimerized propylene oligomers such as $C_8$ and $C_9$ olefins. The higher aliphatic olefins can be saturated to provide fuel or plasticizer components.

It is highly desirable to operate the oligomerization reaction under plug flow conditions to assure uniform conversion along the reaction front. Maintenance of plug flow conditions assures a tighter product distribution. Without plug flow conditions, channeling and even recirculation can result. In "channeling", segments of the reaction front move downwardly more quickly than other segments of the reaction front causing bypassing of downstream product fluid by the upstream reactor fluid. This flow instability is also called "fingering" and is a result of the fluid wanting to achieve a lower energy state. "Recirculation" involves swirling of the reactants against the direction of flow. Channeling can cause underconversion and overconversion of reactants to product; whereas, recirculation can have the same effect but to a greater degree. Overconversion can generate even greater temperatures than desired for the oligomerization reaction to proceed and can cause the catalyst to degrade by deposition of carbon particles on the catalyst which is a phenomenon known as "coking". These effects operate to spread the product distribution away from desired products, thereby diminishing product value and consistency.

It was originally thought that a downflow reactor scheme would provide sufficient reaction front stability to operate under plug flow conditions. Pilot plant studies did not alert to the fact that plug flow could not be maintained under downflow oligomerization conditions. Modeling was conducted to study the stability, of the reaction front under oligomerization conditions. The study revealed not only that downflow aliphatic oligomerization would be unstable, but that it would be far less stable than anticipated. Surprisingly, the modeling study revealed that downflow, was so unstable that channeling and even recirculation of reactants could take place under certain conditions.

The density of the liquid mixture in the aliphatic oligomerization reaction decreases proportionally with the progress of the oligomerization. The relatively high heat of reaction from oligomerization generates very high temperatures causing the reaction products to be less dense and more buoyant relative to the reactants even though the higher aliphatic olefin products are more dense than the lower aliphatic olefin reactants at equivalent conditions. The higher temperature effects a greater reduction in density than the composition change increases the density of the products. The viscosity of the liquid mixture in the oligomerization also decreases proportionally with progress of the oligomerization, but the effect of viscosity on stability is much less prominent than is the effect of density. Flow instability occurs when the denser inlet fluid bypasses the less dense product fluid during operation in downflow.

Upflow reactors with and without fixed catalyst beds are disclosed in the art. U.S. Pat. No. 5,789,640 discloses an upflow fluidized bed system using solid acid catalysts. U.S. Pat. No. 4,255,352 discloses upflow through a series of tank reactors to react an olefinic hydrocarbon and an olefinically unsaturated nitrile in the presence of a diluent predominantly comprising water to produce unsaturated dinitriles. The latter patent discloses the use of promoters which it defines to include catalysts without discussion of fixing the catalyst bed. U.S. Pat. No. 6,013,845 discloses producing bisphenol from dimethyl ketone and phenol in a fluidized catalyst bed. Backmixing of catalyst and the reactor feed is minimized by packing the bed with randomly oriented packing.

Both U.S. Pat. No. 3,560,167 and U.S. Pat. No. 4,801,432 disclose upflow reactors with fixed catalyst beds. Both reactors are equipped for at least one gaseous reactant, although the reactions take place partially in the liquid phase, and mechanical hold-down structures are required to maintain the stability of the catalyst bed.

U.S. Pat. No. 4,695,665, U.S. Pat. No. 4,051,191 and U.S. Pat. No. 4,343,957 disclose upflow processes for the production of cumene using solid phosphoric acid in fixed catalyst beds. The advisability of using an upflow scheme for an oligomerization reaction of aliphatic olefins to obtain plug flow conditions is not disclosed, nor is there any indication of the extent of the instability of an aliphatic oligomerization reaction proceeding in downflow mode.

It is an object of this invention to improve the plug flow stability and product distribution of an aliphatic olefin oligomerization reaction by operating the reaction in an upflow mode.

BRIEF SUMMARY OF THE INVENTION

It has been surprisingly found that operating an oligomerization of lighter aliphatic olefins in the presence of a solid acidic catalyst and heavy paraffins in an upflow mode enables maintenance of plug flow conditions far better than operation of the oligomerization in the downflow mode. It was not even understood until modeling experimentation was undertaken how poorly the oligomerization of lighter aliphatic olefins would proceed in downflow mode.

Accordingly, an embodiment of the present invention comprises an oligomerization process for the production of higher aliphatic olefins. The process comprises passing a liquid oligomerization feed stream comprising lighter aliphatic olefins to a reactor vessel. The liquid oligomerization feed stream is transported upwardly in the reactor vessel against gravity through a fixed bed of solid oligomerization catalyst under oligomerization conditions. The catalyst has a Hammett acidity value of −4 or less. A liquid saturate stream comprising paraffins is passed into contact with the feed stream and the catalyst. A liquid oligomerization effluent stream comprising paraffins and product higher aliphatic olefins is then recovered.

In another embodiment of the present invention, the feed stream comprises $C_3$ or higher aliphatic olefins, the catalyst is a solid phosphoric acid catalyst, the liquid saturate stream comprises $C_5$ or higher paraffins and the liquid oligomerization effluent stream comprises $C_6$ or higher aliphatic olefin product.

In a further embodiment of the present invention, the oligomerization feed stream has a first density and the oligomerization effluent stream has a second density that is less than the first density of the oligomerization feed stream.

In still further embodiments of the invention, the oligomerization conditions include a temperature of 93° to 260° C. (200° to 500° F.), a pressure of 690 to 10342 kPa (100 to 1500 psig) and a liquid hourly space velocity of 0.5 to 5 $hr^{-1}$. Preferably, the oligomerization conditions include a temperature in the range of 149° to 232° C. (300° to 450° F.).

In even further embodiments of the invention, the oligomerization effluent stream is passed to a separator and separated into a product stream comprising higher aliphatic olefins and paraffins or at least a portion of the paraffins is recycled to the reactor vessel. Additionally, in an embodiment, at least a portion of the saturate stream enters the reactor vessel with the feed stream.

In other embodiments of the invention, it is contemplated that oligomerization will occur predominantly in the liquid phase, that the reactor vessel will include more than one fixed catalyst bed or that an inert material is disposed in the reactor vessel between a fixed bed of catalyst and a reactor feed inlet.

Moreover, other additional embodiments of the invention include that the lighter aliphatic olefins include butenes, the paraffins in the saturate stream have a carbon number of at least 6 or the product higher aliphatic olefins include octenes. Additionally, an embodiment of the invention contemplates that the product higher aliphatic olefins comprise dimerized or trimerized lighter aliphatic olefins.

Other objects, embodiments and details of this invention will be provided in the following detailed disclosure of the invention.

DETAILED DESCRIPTION OF THE INVENTION

Figure 1:
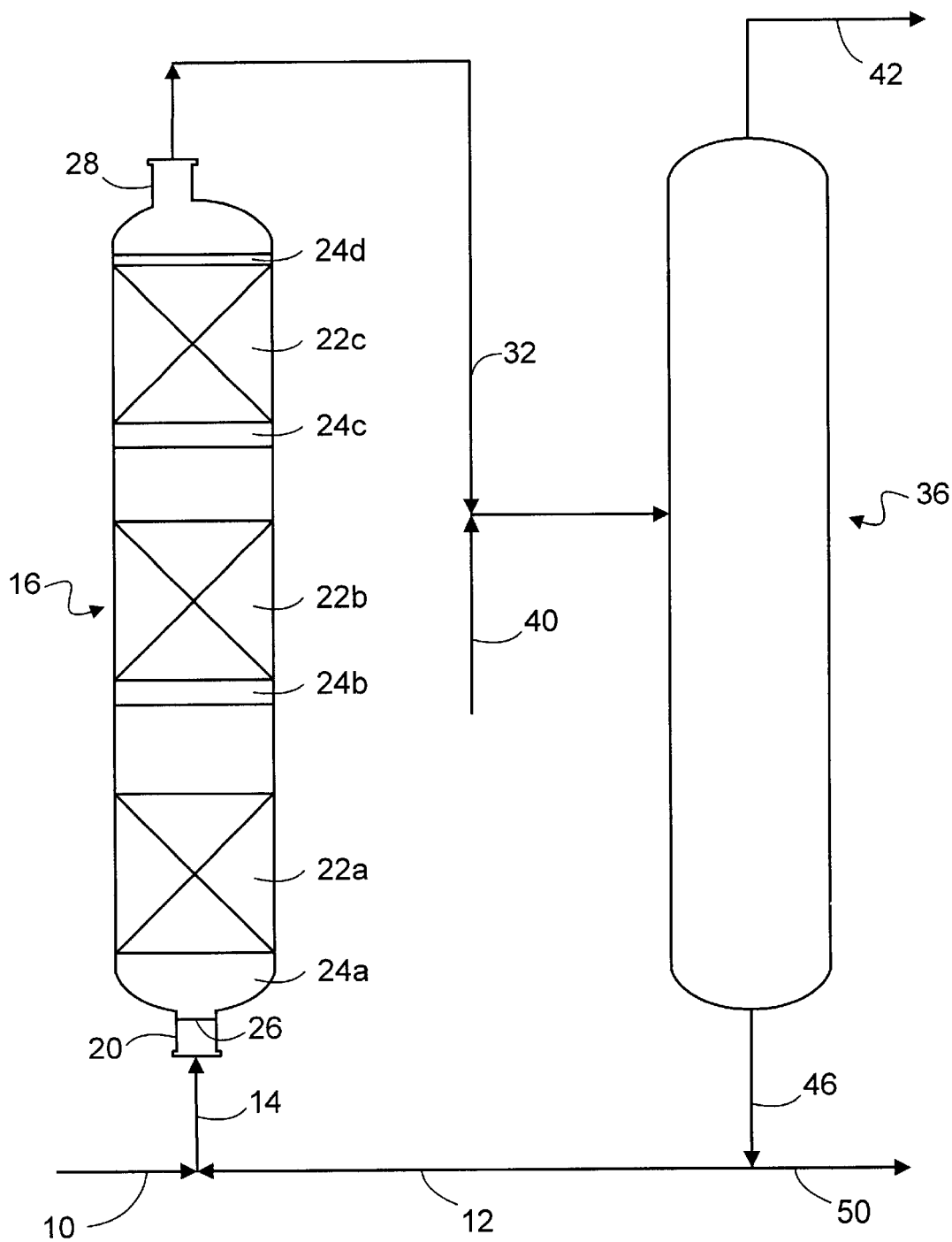
FIG. 1 is a process flow diagram of the present invention.

The essential operational zone for the practice of this invention is the oligomerization reaction zone. Suitable oligomerization zones for this invention take on many forms. The oligomerization process is known by many names such as catalytic condensation and also catalytic polymerization. Known catalysts for effecting such reactions include heterogeneous catalyst such as solid acids and homogenous catalysts, in particular halogenated catalysts such as boron trifluoride as described in U.S. Pat. No. 3,906,053, U.S. Pat. No. 3,916,019 and U.S. Pat. No. 3,981,941.

Preferred catalyst for the oligomerization reaction can generally be described as protonic acids. The preferred acids will generally have a Hammett acidity function of −4.0 or less. Examples of catalysts-falling into this category include ion exchange resin catalysts, such as sulfonated ion exchange resins, and phosphoric acid catalysts. A particularly preferred catalyst is a solid phosphoric acid ("SPA") catalyst which has a Hammett acidity function of approximately −5.0 or lower. The SPA catalyst refers to a solid catalyst that contains as a principal ingredient an acid of phosphorous such as ortho-, pyro- or tetraphosphoric acid.

SPA catalyst is normally formed by mixing the acid of phosphorous with a siliceous solid carrier to form a wet paste. This paste may be calcined and then crushed to yield catalyst particles where the paste may be extruded or pelleted prior to calcining to produce more uniform catalyst particles. The carrier is preferably a naturally occurring porous silica-containing material such as kieselguhr, kaolin, infusorial earth and diatomaceous earth. A minor amount of various additives such as mineral talc, fuller's earth and iron compounds including iron oxide may be added to the carrier to increase its strength and hardness. The combination of the carrier and the additives preferably comprises about 15–30% of the catalyst, with the remainder being the phosphoric acid. The additive may comprise about 3–20% of the total carrier material. Variations from this composition such as a lower phosphoric acid content are however possible. Further details as to the composition and production of SPA catalysts may be obtained from U.S. Pat. No. 3,050,472, U.S. Pat. No. 3,050,473 and U.S. Pat. No. 3,132,109 and from other references.

Oligomerization zones in general are maintained at conditions which may vary widely due to the previously listed variables. In this invention, the oligomerization reaction zone is preferably operated at temperatures and pressures that increase the compatibility of its effluent conditions with the inlet conditions of the saturation reaction zone inlet and its inlet conditions with the dehydrogenation reaction zone effluent conditions. The preferred temperature of the oligomerization reaction zone may be in a range of from 38° to 260° C. (100° to 500° F.), will typically be in a range of from 93° to 260° C. (200° to 500° F.), and will more typically be in a range of from 149° to 232° C. (300° to 450° F.). Pressures within the oligomerization reaction zone will usually be in a range of from 690 to 8274 kPa (100 to 1200 psig) and more typically in a range of from 1379 to 6895 kPa (200 to 1000 psig). When practicing this invention the preferred operating pressure for the SPA catalyst will be in a range of from 690 to 10342 kPa (100 to 1500 psig) and more typically in a range of from 1379 to 6895 kPa (200 to 1000 psig) with pressures of 1379 to 3447 kPa (200 to 500 psig): being particularly preferred. Oligomerization conditions may also include a liquid hourly space velocity (LHSV) of 0.5 to 5 hr$^{-1}$. It has also been found that maintaining operating temperatures in a narrow range of from 149° to 204° C. (300° to 400° F.) can push selectivity toward the production of more $C_8$ isomers when $C_4$ is in the feed.

The feed to the oligomerization zone reaction will typically comprise $C_3$ to $C_5$ aliphatic olefins, but may comprise olefins have carbon numbers of 12 or higher. Steam or water may be fed into the reactor to maintain a low water content for hydration of the preferred SPA catalyst. The source of the olefin feeds are typically a light gas stream recovered from the gas separation section of an FCC process, $C_4$ streams from steam cracking and coker off gas, $C_3$ streams such as from a separator section of a modified FCC process or the effluent from a dehydrogenation zone. In most operations, this olefin feed stream will contain at least 10 wt-% $C_4$ olefins but it may also constitute all or substantial quantities of $C_3$ olefins. Typically the olefin feeds can, have a $C_3$ to $C_5$ olefin concentration of at least 30 wt-%. Where $C_4$ olefins are predominant in the feed, the principal oligomerization products comprise $C_8$ and heavier olefins. Where $C_3$ olefins are predominant in the feed, these olefins will primarily combine to produce $C_9$ and higher olefins. Preferred feeds will have a concentration of at least 30 wt-% and more preferably at least 50 wt-% total olefins in the feed stream. The olefin content of the feed may predominately comprise normal olefins of a single carbon number.

In the practice of this invention, a saturate stream comprising paraffin components contact the catalyst in conjunction with the usual oligomerization zone feed. The paraffin components will preferably comprise heavy hydrocarbons having at least 6 carbon atoms, preferably at least 7 carbon atoms, and more preferably at; least 8 carbon atoms. Paraffin components having up to 20 carbon atoms may be used and will preferably comprise paraffins having a substantially different carbon number than the product oligomers. Cycloparaffins are also suitable components for the saturate stream with cyclohexane being preferred.

The presence of the heavy paraffins promotes liquid phase conditions in the oligomerization zone. The combined heavy saturate stream and feed will usually maintain at least partial liquid phase conditions in the oligomerization zone. Preferably, essentially all, i.e. at least 90 wt-%, of the fluid in the oligomerization zone will be in liquid phase.

The effective washing action of the heavy hydrocarbons requires a minimum liquid mass flux. Preferred rates for the liquid mass flux will exceed 14,648 kg/hr/m$^2$ (3000 lb/hr/ft$^2$). However, if the preferred SPA catalyst is used, the liquid mass flux rate should not be so high that the fluid velocity exceeds 3.07 meters per second (10.07 feet per second) or a mechanical hold down structure would have to be installed in the reactor vessel to prevent the fluid flow from urging the catalyst bed upwardly.

The heavy paraffin components may enter the process with or separately from the incoming feed or may be injected into an oligomerization reaction zone at intermediate locations within a single catalyst bed or a number of catalyst beds. It is preferred to have the heavy paraffins present as the feed initially enters the reaction zone to maximize the benefit of the heavy paraffins in the process. In such cases, it is typical to have at least 40 wt-% and more often 50 wt-% or more of the total saturate stream enter the first reactor with the feed. Additional quantities of the heavy paraffins may be injected in stages through the process to maintain temperature control throughout the bed or beds of oligomerization catalyst.

The oligomerization zone preferably has a multiple bed arrangement. The catalyst beds are preferably contained within one or more cylindrical, vertically oriented vessels. The catalyst is preferably disposed in fixed beds within the oligomerization zone in what is known as a chamber-type reactor structure. In a chamber-type reactor, the reactants flow through a series of large diameter catalyst beds. Typically, a chamber-type reactor will contain about five catalyst beds. The temperature of the reactants may be further controlled by recycling to the catalyst beds the relatively inert paraffin saturate stream which acts as a heat sink. Oligomerization reaction zones are routinely arranged with such multiple beds of catalyst that receive an intermediate injection of a quench material to control temperatures from the exothermic reaction. Substantial advantage can be obtained by adding the heavy paraffins as an intermediate injection stream that also benefits the process by serving as a quench stream.

With the addition of the saturate stream, the combined feed to the oligomerization zone will preferably have a ratio of paraffins to olefins of from 1:1 to 5:1. Thus the overall paraffin concentration of the feed to the oligomerization reaction zone will typically be at least 50 wt-% and more typically at least 70 wt-%. The olefin conversion will typically range from 80 to 99 wt-%.

The effluent from the oligomerization reaction zone will normally enter a separator. Separation of the effluent stream from the oligomerization zone will at minimum recover the heavy paraffins from the effluent for recycle to the oligomerization zone. The usual separator for recovery of the product oligomers also recovers unreacted feed as an overhead stream and at least a portion of the saturate stream for recycle to the oligomerization zone. The heavy paraffins may be recovered with the product stream or the unreacted feed olefins and recycled to the oligomerization zone.

The source of the heavy paraffins for transport to the oligomerization zone can be any stream that can supply the higher carbon number paraffins in the necessary quantities. The paraffins can be imported into the process from external sources or produced by saturating all or a portion of the oligomerization effluent stream. (Unless otherwise noted the term "portion" when used herein to describe a process stream refers to either an aliquot portion of the stream or a dissimilar fraction of the stream having a different composition than the total stream from which it was derived.) The entire effluent from the oligomerization zone may be saturated to provide a source of recycle paraffins for the process as well as saturated oligomers. Alternatively, the effluent may be separated as described to recover the portion of the paraffins that are recycled to the oligomerization zone.

It was found to much surprise that this oligomerization reaction does not provide a stable plug flow condition in downflow mode. Indeed, Computational Fluid Dynamic modeling revealed, despite no indication from pilot plant operation, that channeling can occur during oligomerization in downflow mode, thereby disrupting plug flow conditions. It was also found under certain conditions that the liquid flowing through fixed catalyst beds could even recirculate, that is, begin to flow upwardly in a downflow reactor scheme. These types of non-plug flow conditions can cause both underconversion and overconversion of the reactants which spreads the product distribution and can cause higher reaction temperatures which would operate to degrade the catalyst. However, it was found that operation of the oligomerization in an upflow scheme maintains plug flow conditions and avoids these surprisingly severe problems.

All other things being equal, an upflow reactor will require no more energy consumption than a downflow reactor of similar design. In a downflow reactor, the reactants must be pumped through a line outside of the reactor to the top of the reactor to the reactor inlet and pumped downwardly through the catalyst beds in the reactor. Whereas, in the upflow reactor, the reactants will have to be pumped from the bottom of the reactor through the catalyst beds to the outlet at the top of the reactor which is at the same relative height as the reactor inlet of the downflow reactor. It is believed that the same pressure will be required to pump fluid to the top of the downflow reactor and down through the downflow reactor as from the bottom of the upflow reactor to the top of the upflow reactor.

The process and different operational steps will be described in conjunction with the process flow diagram in FIG. 1. FIG. 1 shows only limited forms of the invention and only those portions of the process that are necessary to gain an understanding of the invention and the necessary means of integrating the principal processing steps that comprise the invention. Further details related to valves, control means, pumps, compressors, coolers and other necessary processing equipment are well known to those skilled in the art and not described in detail unless necessary for an understanding of the invention.

FIG. 1 shows an oligomerization feed stream, rich in lighter aliphatic olefins brought into the process by line 10 and combined with a recycle stream of paraffins carried by line 12. Line 10 may carry oligomerization feed from a dehydrogenation, zone (not shown) but other previously mentioned sources of feed are also suitable. Line 14 carries the combined feed and recycle paraffin stream into oligomerization reactor vessel 16 through an inlet nozzle 20 wherein the feed and paraffins contact a catalyst in beds 22a–c. Any type of reactor used to react reactants in the presence of catalyst is generally suitable in practicing this invention. However, cylindrical reactors are preferred for their simplicity. Reactor vessel 16 can comprise tubing, pipes, jets or other common means for introducing reactants into the reaction zone of the reactor. It may be preferable to introduce feed and/or saturate at higher levels in the reactor vessel, such as at the catalyst beds by interbed distributors (not shown). Additionally, it may also be preferable to bring the saturate stream and the feed stream into the reactor vessel by different lines.

Preferably, the bottom portion of the reactor is filled with aggregate 24a. The amount of such aggregate is not critical to the invention. However, sufficient aggregate should be present to provide support to the reactor internals and disperse the flow of reactants such that plug flow is achieved at the inlet to the catalyst bed. This aggregate can comprise any material which will not easily fluidize and is essentially inert to the reactants and products produced in the reactor.

Preferably, this aggregate is comprised of alumina balls. Crushed firebrick and inert ceramic balls are also suitable. Catalyst beds 22a–c are packed above each respective layer of aggregate 24a–c. A plate 26 disposed in the nozzle 20 to support the aggregate 24a may be configured to facilitate fluid distribution. An aggregate layer 24d may also be disposed above the top catalyst bed to minimize the potential for catalyst fluidization. A structural hold-down plate (not shown) may also be installed over the top of the aggregate layers 24b–d to further withstand catalyst fluidization. Preferably, about 10 to about 50% volume of the reactor is taken up by catalyst as determined when dry.

Stream 32 carries an oligomerization effluent comprising higher aliphatic olefins and paraffins out the outlet nozzle 28 to separator 36. Line 40 adds a make-up stream of paraffins to the effluent entering separator 36. Separator 36 removes a heavy fraction of paraffins from the higher oligomers formed in the oligomerization zone. Separator 36 may provide a simple flashing operation to make a rough cut of the heavy stream or may be a fractionation zone. Overhead stream 42 carries the higher aliphatic olefins from separator 36 for further processing. Such further processing may include saturation of the olefins in a saturation zone. A bottoms stream containing paraffins for recycle to the process is withdrawn by line 46. A good separation is desired to minimize the carry-over of higher aliphatic olefins to the oligomerization zone. A portion of bottoms stream 46, which is typically equal to the mass flow of the make-up paraffin addition from line 40, is purged from the process by line 50 to reduce the build up of higher aliphatic olefins in the recycle stream. The remainder of the heavy paraffins is returned for admixture with incoming feed via line 12.

To more fully demonstrate the attendant advantages of the upflow oligomerization scheme of the present invention over the downflow scheme, the following modeling results are described.

EXAMPLE 1

A comparison was made of an upflow oligomerization process versus a downflow oligomerization process using Computational Fluid Dynamics modeling. The upflow reactor was assumed to have a diameter of 2.9 meters and a catalyst bed height of 2.5 meters. A constant heat release was assumed along the axial length of a catalyst bed. The density and viscosity of the liquid were made a function solely of temperature.

It was assumed that only butylene would be in the feed stream as a reactant with the remainder being paraffin diluent. Inlet conditions included mass fractions of isobutylene at 0.1191, of normal butylene at 0.1889 and paraffin diluent, comprising mostly octanes, at 0.6920. Moreover, the inlet temperature was assumed to be 103° C. and the outlet temperature was assumed to be 126° C. The inlet velocity was assumed to be 1.03 meters per second. The inlet viscosity was calculated to be $1.44 \times 10^{-4}$ kg/m/s and the inlet density was calculated to be 567 kg/m$^3$. The outlet viscosity was calculated to be $1.25 \times 10^{-4}$ kg/m/s and the outlet density was calculated to be 533 kg/m$^3$.

Figure 2:
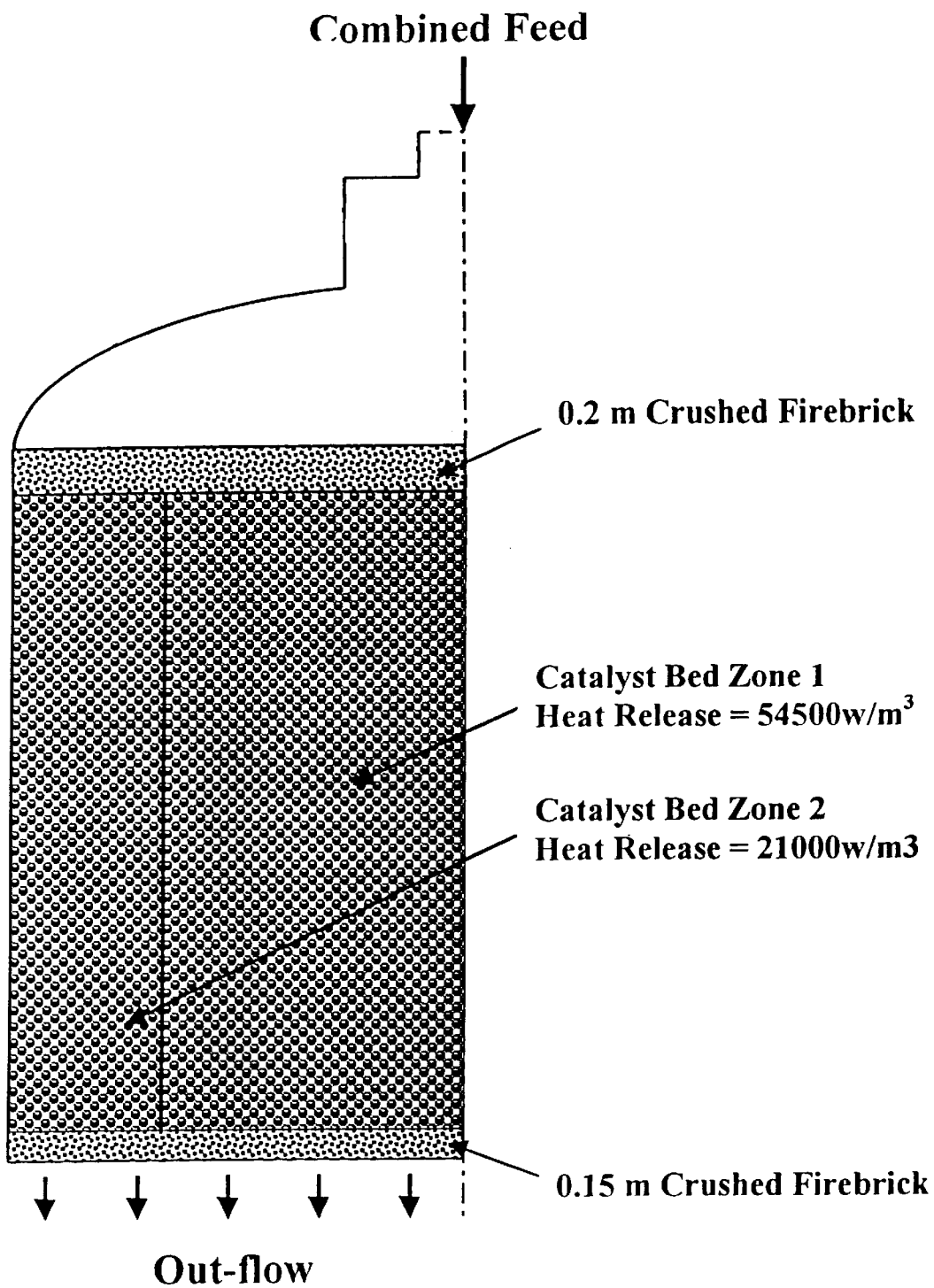
FIG. 2 is a schematic cross-section of half of a catalyst bed in a downflow reactor upon which flow modeling was based assuming constant axial heat release.

FIG. 2 shows the half-section of a downflow reactor upon which the modeling was based. To promote a disparity along the radial displacement in the reactor catalyst bed, catalyst bed zone 1 was assumed to have a heat release of 54,500 watts per cubic meter whereas the outer radial catalyst bed zone 2 was assumed to have a heat release of 21,000 watts per cubic meter closer to the outside of the reactor. The radius of the boundary between zone 1 and zone 2 was set at 1.02 meters to equalize the respective volumes of the zones. The same conditions were also assumed for modeling with respect to an upward flow reactor as shown in FIG. 3.

Figure 3:
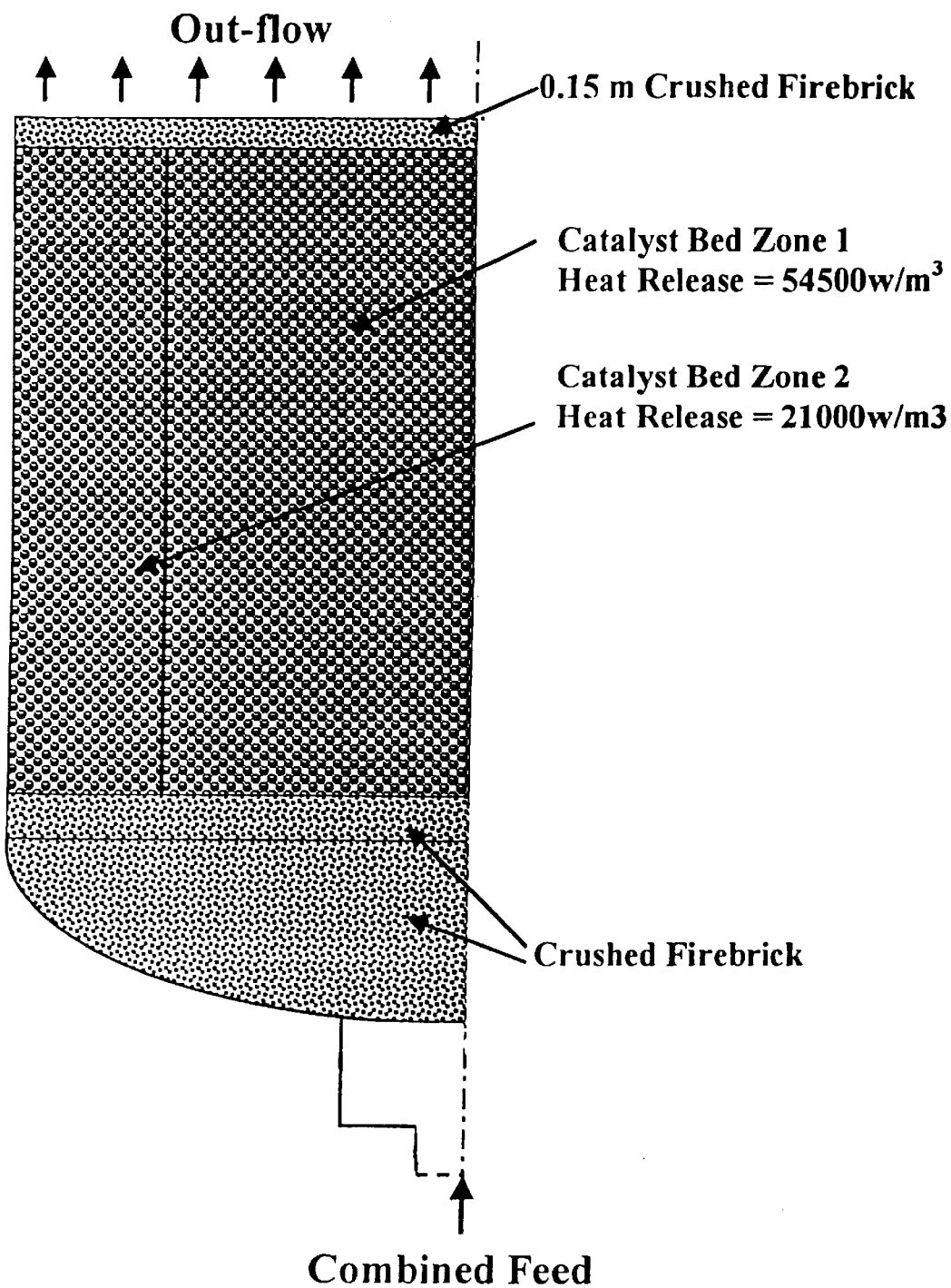
FIG. 3 is a schematic cross-section of half of a catalyst bed in an upflow reactor upon which flow modeling was based assuming constant axial heat release.
Figure 4:
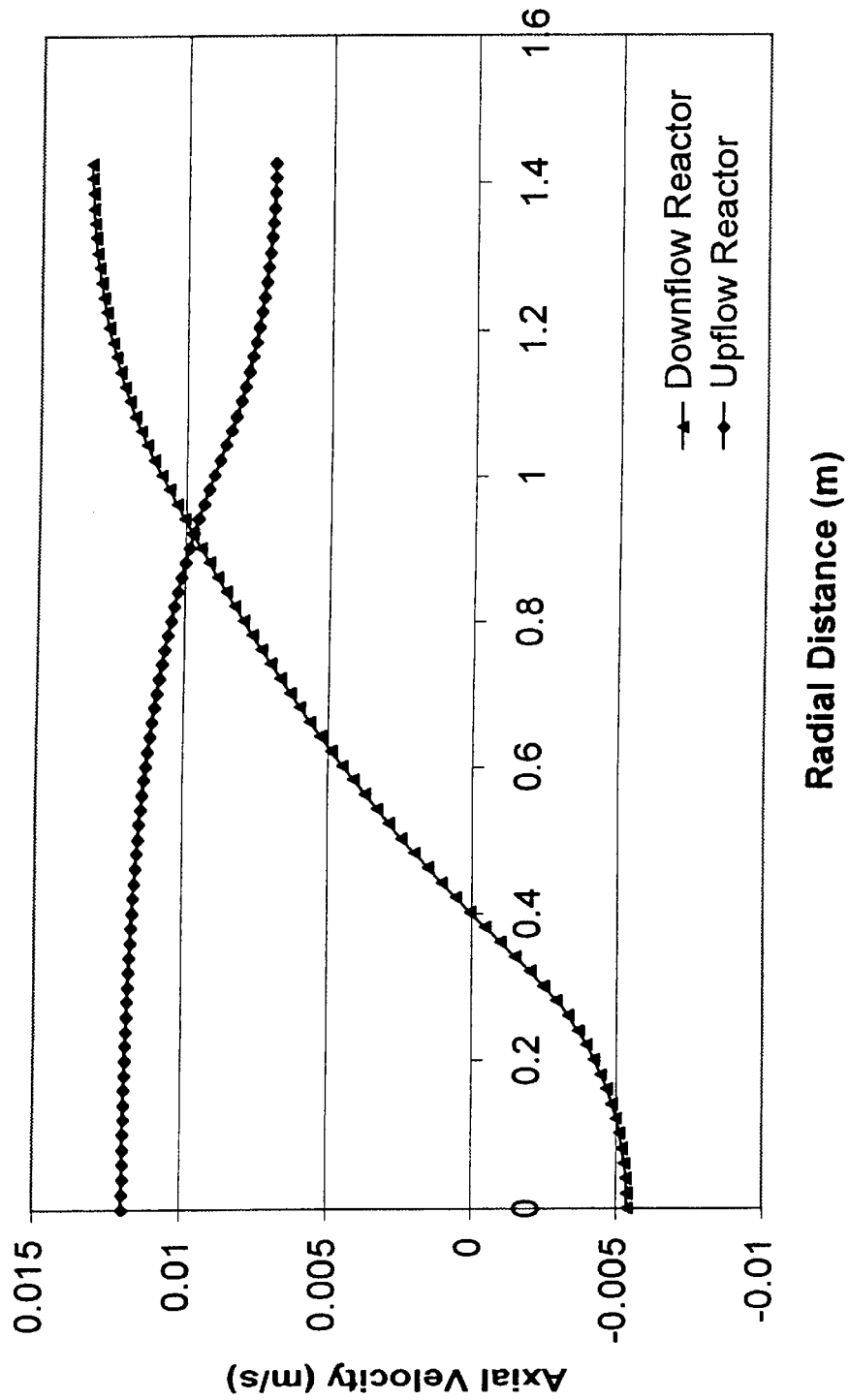
FIG. 4 is an axial velocity radial profile comparing the models represented in FIGS. 2 and 3.

FIG. 4 is a plot of the axial velocity radial profile at 0.3 meters from the outlet of the catalyst bed comparing the upflow reactor scheme in FIG. 3 to the downflow reactor scheme in FIG. 2. In the plot of axial velocity as a function of radial distance from the center of the reactor, the axial velocity slows to 0 at 0.4 meters and begins to have a negative axial velocity near the center of the reactor. This indicates that not only is there bypassing of liquid along the front of the reaction, thereby destroying plug flow reaction conditions, but that some of the reactants are actually recirculating, i.e., flowing upwardly in a downflow reactor. Consequently, much of the feed stream reactants will spend a longer residence time in the reactor in contact with the catalyst which can cause over-oligomerization, thereby generating olefins with higher carbon numbers than desired. Moreover, the excessive residence times can generate more heat from reactions and cause coke to deposit on the catalyst, thereby degrading catalyst performance. On the other hand, the upflow reactor exhibits a fairly steady axial velocity, right around 0.01 meters per second, along the radial profile. The axial velocity dips below 0.01 meters per second at about 0.9 meters which may account for the smaller heat release in zone 2 which boundary is set at 1.02 meters. However, the disparate heat release between zones 1 and 2 in the upflow reactor only manifests a slight change in axial velocity, thereby maintaining close to plug flow conditions. The advantage of the upflow reactor versus the downflow reactor in liquid phase conditions was surprisingly significant.

Figure 5:
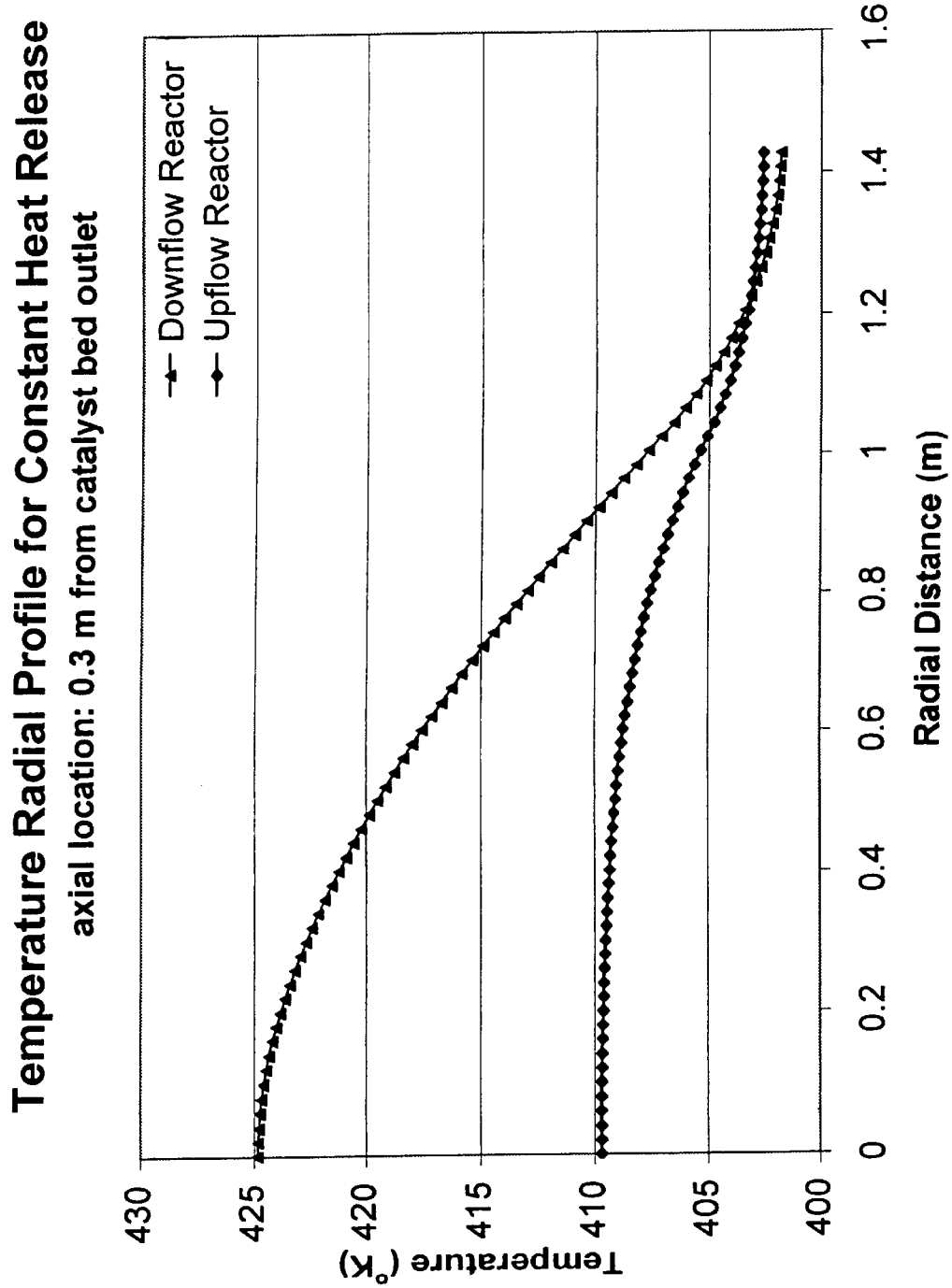
FIG. 5 is a temperature radial profile for constant heat release comparing the models represented in FIGS. 2 and 3.

FIG. 5 shows a comparison of the temperature radial profile for the upflow reactor versus the downflow reactor. The downflow reactor exhibits over about a 23° C. temperature variation between the center and the wall of the reactor. Whereas, the temperature radial profile for the upflow reactor does not vary more than about 7.5° C. The extent of the improvement in the temperature stability of the upflow reactor versus the downflow reactor was also surprising.

EXAMPLE 2

Figure 6:
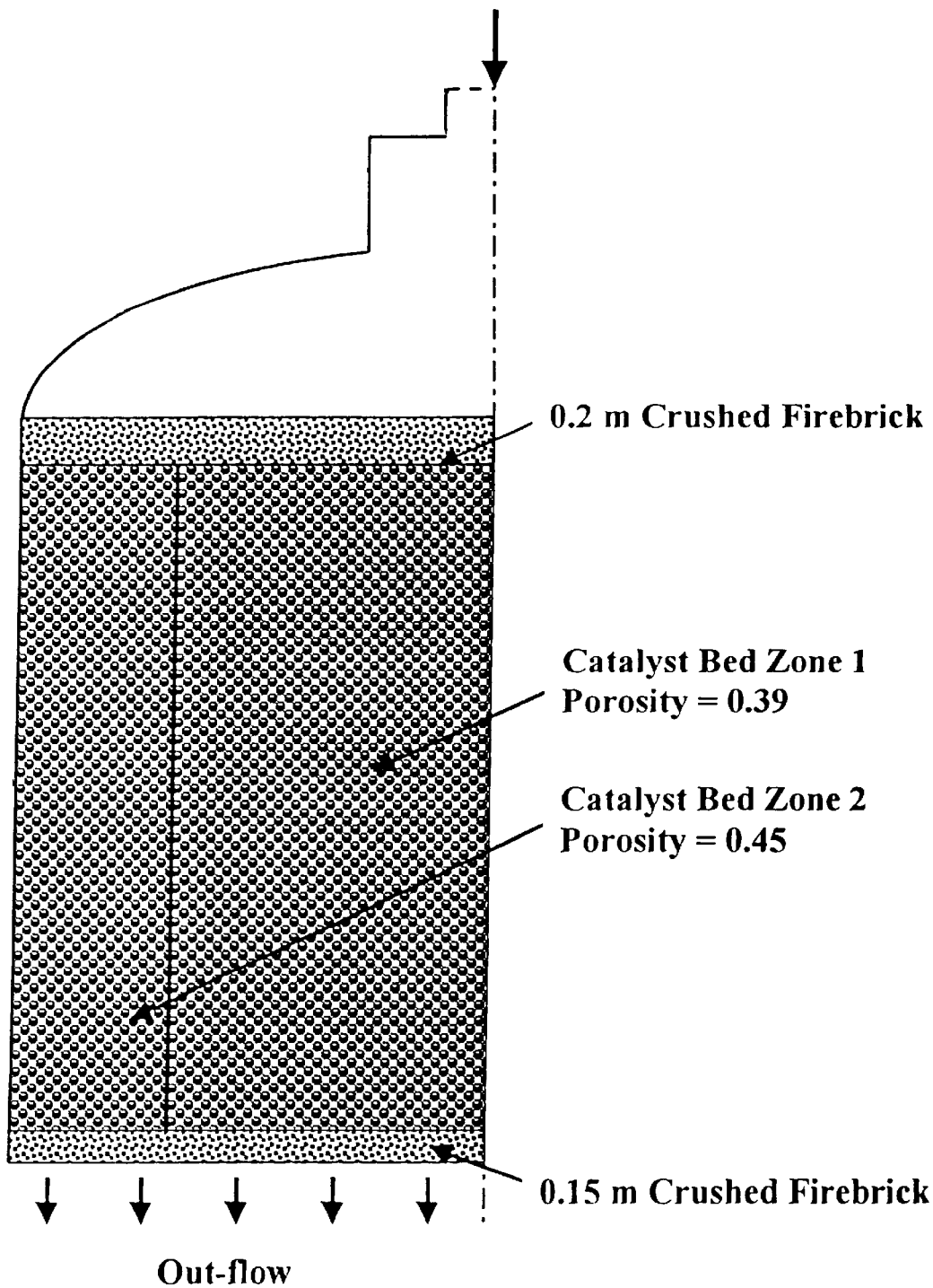
FIG. 6 is a schematic cross-section of half of a catalyst bed in a downflow reactor upon which flow modeling was based accounting for reaction kinetics.
Figure 7:
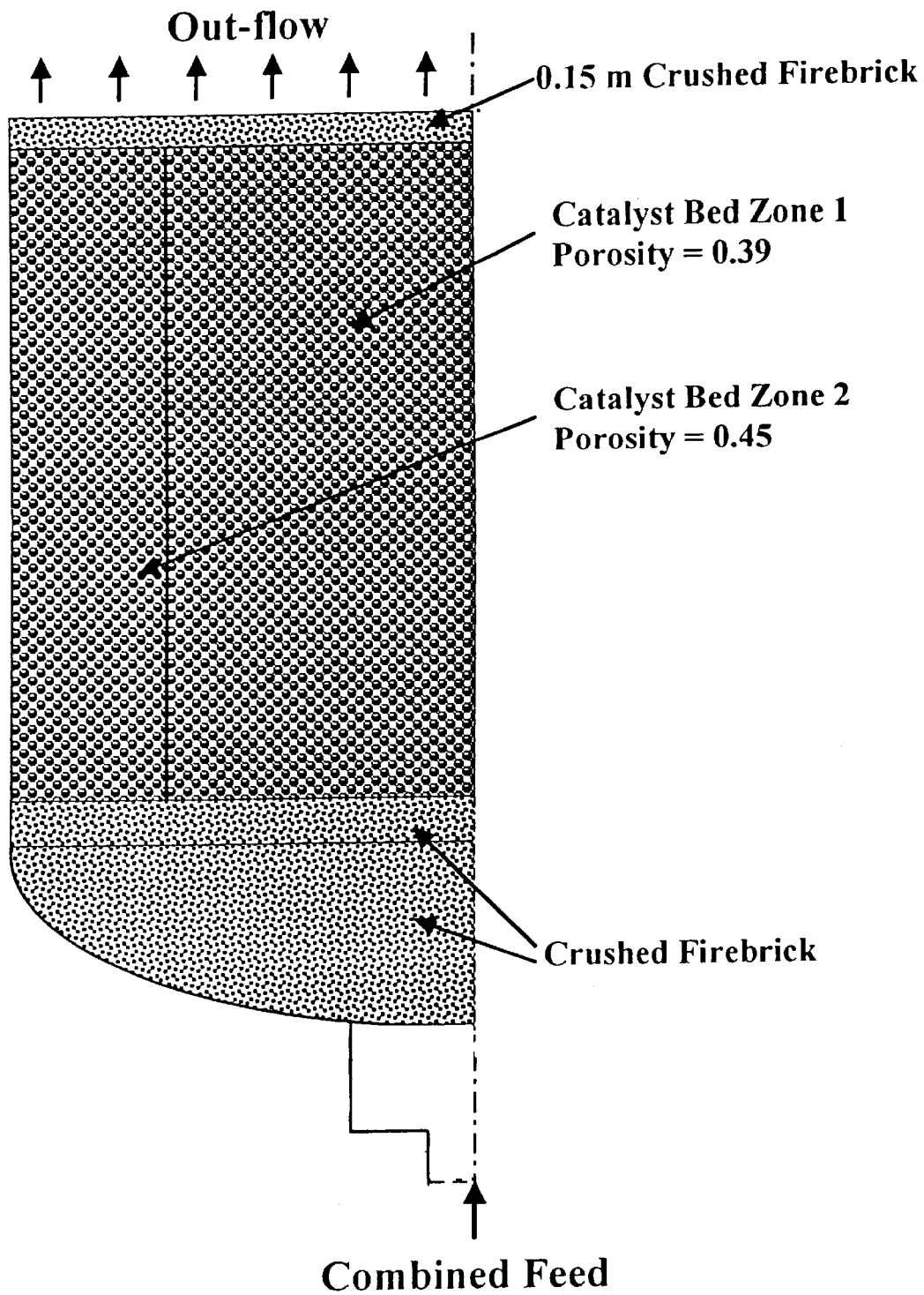
FIG. 7 is a schematic cross-section of half of a catalyst bed in an upflow reactor upon which flow modeling was based accounting for reaction kinetics.

An additional study was conducted using Computational Fluid Dynamics modeling in which reaction kinetics, density, viscosity and heat capacity of the liquid mixture were made functions of both temperature and composition. The model for the downflow reactor is illustrated in FIG. 6, whereas the model for the upflow reactor is shown in FIG. 7. The upflow reactor was assumed to have a diameter of 2.9 meters and a catalyst bed height of 2.5 meters.

It was assumed that only butylene would be in the feed stream as a reactant with the remainder being paraffin diluent. Inlet conditions included mass fractions of isobutylene at 0.1191, of normal butylene at 0.1889 and paraffin diluent, comprising mostly octanes, at 0.6920. Moreover, the inlet temperature was assumed to be 103° C. and the inlet velocity was assumed to be 1.03 meters per second. The inlet viscosity was calculated to be $1.44 \times 10^{-4}$ kg/m/s and the inlet density was calculated to be 567 kg/m$^3$. To approximate the reaction kinetics, it was assumed that three reactions would occur in the oligomerization:

(1) 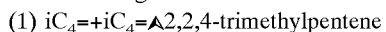
(2) 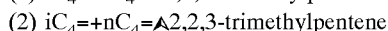
(3) 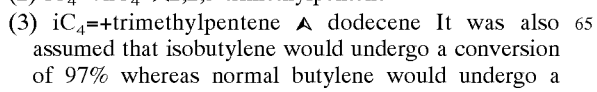 It was also assumed that isobutylene would undergo a conversion of 97% whereas normal butylene would undergo a conversion of 25%. Moreover, it was assumed that 5% of the reaction heat would be lost through the wall of the reactor. To simulate a disparity in the reactor, zone 1 of the catalyst bed was given a porosity of 0.39 whereas zone 2 of the catalyst bed was given a porosity of 0.45. As with Example 1, the boundary between zone 1 and zone 2 was set at 1.02 meters.

Figure 8:
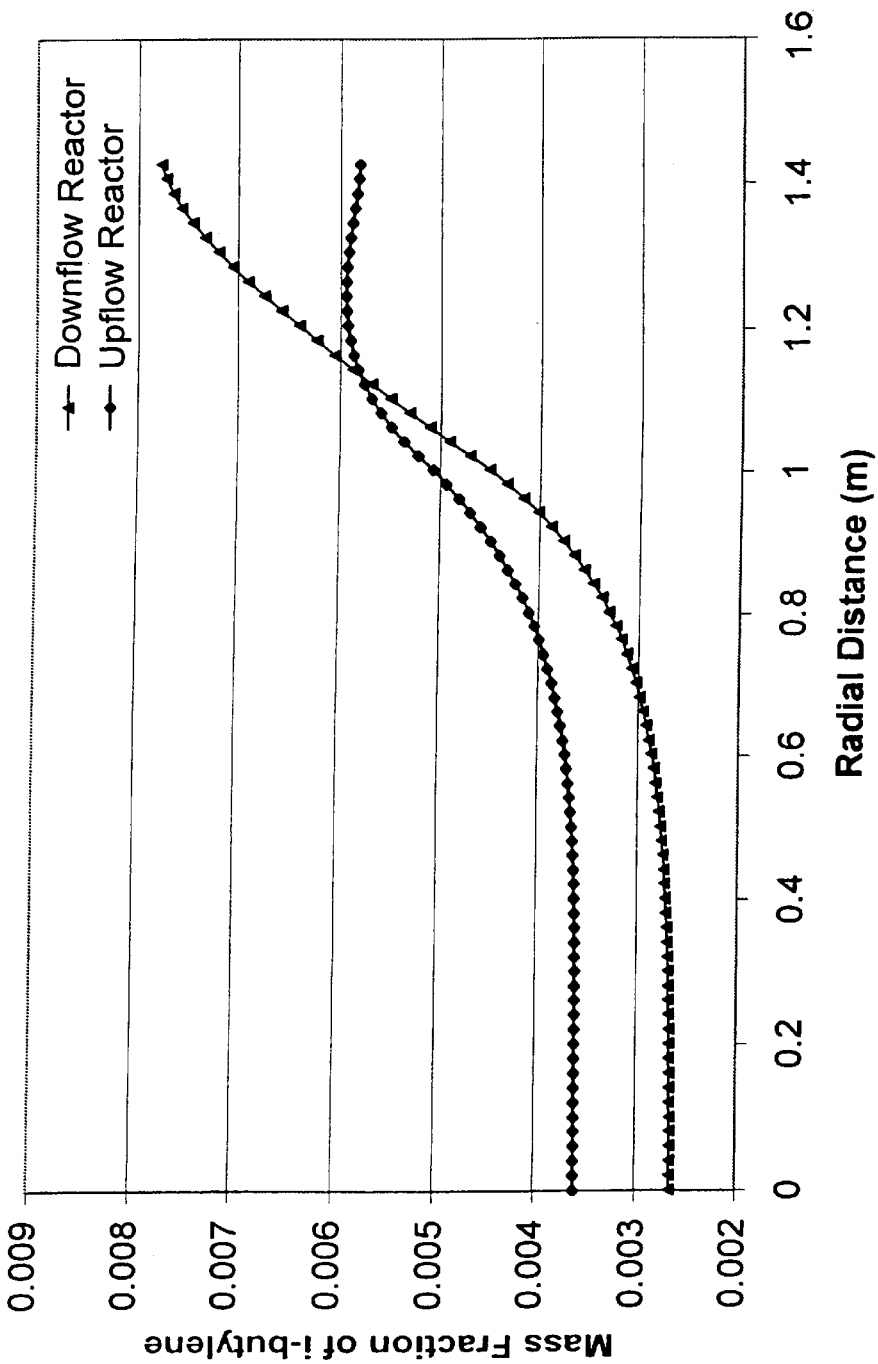
FIG. 8 is a plot of isobutylene radial distribution comparing the models represented in FIGS. 6 and 7.
Figure 9:
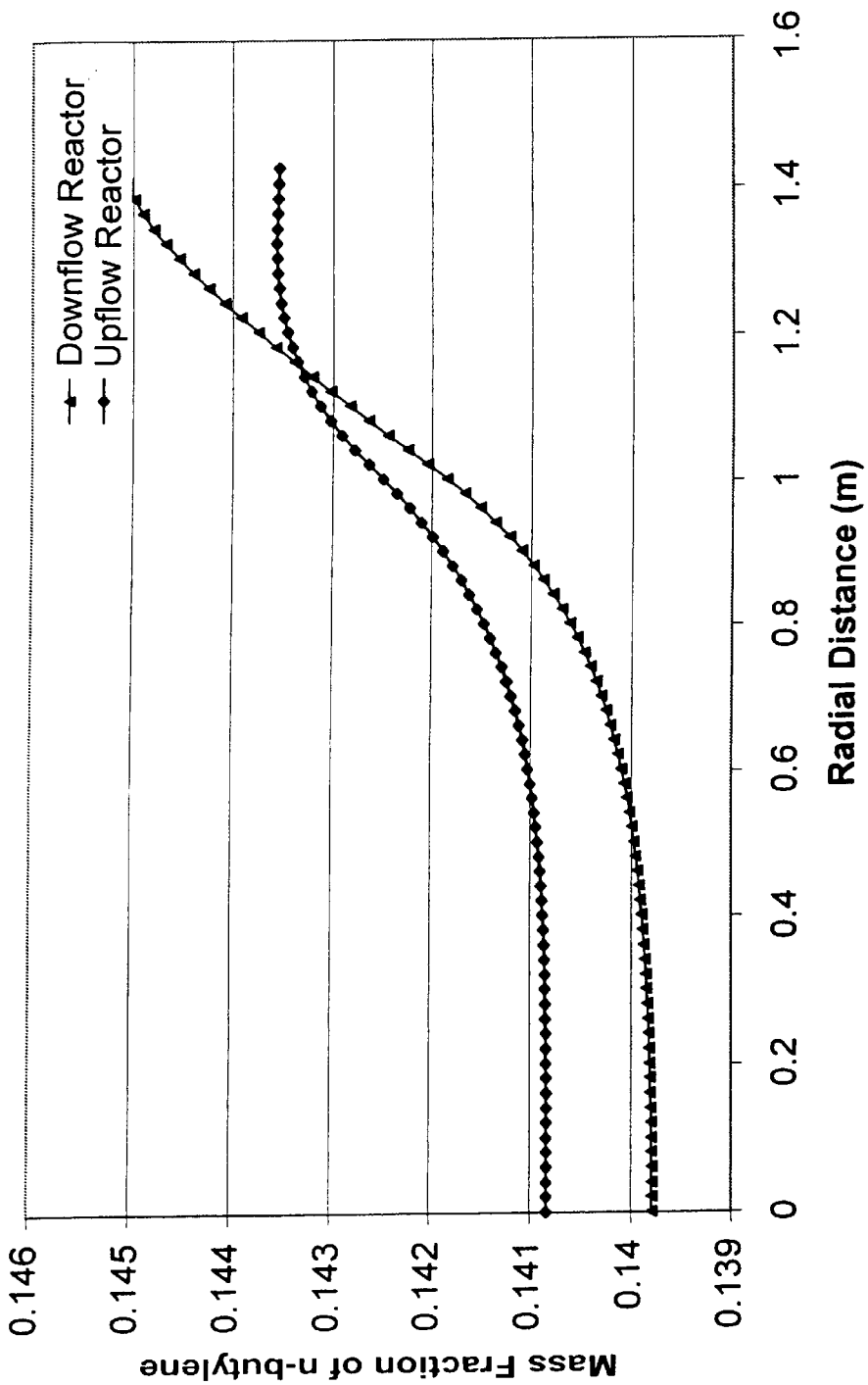
FIG. 9 is a plot of normal butylene radial distribution comparing the models represented in FIGS. 6 and 7.

Results of the model are displayed in FIG. 8 which plots the mass fraction of isobutylene reactant as a function of radial distance from the center of the reactor. The mass fraction distribution of reactant will have a direct impact on the quality of the product distribution. These mass fraction distributions were determined at an axial location of 0.3 meters from the outlet of the catalyst bed. FIG. 8 shows that the radial distribution of mass fraction of isobutylene for the downflow reactor varies widely from about 0.0026 at center to 0.0077 at the wall of the reactor. Whereas, the radial distribution of the mass fraction of isobutylene for the upflow reactor has a tighter distribution from about 0.0036 at the center of the reactor to about 0.0059 at about 1.2 meters from the center of the reactor. The disparate porosity between zone 1 and zone 2 affects the butylene distribution in both flow schemes, but the disturbance in the radial distribution of mass fraction of isobutylene only varies about 64% in the upflow reactor. Whereas, the disturbance in the radial distribution of isobutylene in the downflow reactor is over 196%. Hence, the upflow reactor can handle significant disturbances without substantially destroying plug flow conditions and thereby avoiding substantial degradation of product quality. Under the same disparity, the downflow reactor deviates substantially from plug flow conditions, thereby causing substantial product degradation. The extent of improvement in product distribution of upflow reactor over downflow reactor processes indicated by this model was surprising. Similarly, FIG. 9 shows the radial distribution of the mass fraction of normal butylene as a function of radial distance from the center of the reactor. The downflow reactor exhibited a much wider distribution from 0.1398 at the center of the reactor to about 0.1451 at the wall of the reactor whereas the upflow reactor again exhibited a tighter distribution at about 0.1408 at the center of the reactor to about 0.1435 at the wall of the reactor. This wider distribution for the downflow reactor as compared to the upflow reactor demonstrates that plug flow conditions and, therefore product quality, are much more easily maintained in the upflow reactor when a dramatic porosity disparity is simulated.

What is claimed is:

1. An oligomerization process for the production of higher aliphatic olefins, said process comprising:
   a) passing a liquid oligomerization feed stream comprising lighter aliphatic olefins to a reactor vessel;
   b) transporting said liquid oligomerization feed stream upwardly in said reactor vessel against gravity through a fixed bed of solid oligomerization catalyst under oligomerization conditions, said catalyst having a Hammett acidity value of −4 or less;
   c) passing a liquid saturate stream comprising paraffins into contact with said feed stream and said catalyst; and
   d) recovering a liquid oligomerization effluent stream comprising said paraffins and product higher aliphatic olefins.

2. The process of claim 1 wherein the oligomerization conditions include a temperature of 93° to 260° C. (200° to 500° F.), a pressure of 690 to 10342 kPa (100 to 1500 psig) and a liquid hourly space velocity of 0.5 to 5 hr$^{-1}$.

3. The process of claim 2 wherein said oligomerization conditions include a temperature in a range of from 149° to 232° C. (300° to 450° F.).

4. The process of claim 1 wherein said oligomerization effluent stream is passed to a separator and separated into a product stream comprising said higher aliphatic olefins and paraffins, at least a portion of said paraffins is recycled to said reactor vessel.

5. The process of claim 1 wherein at least a portion of said saturate stream enters said reactor vessel with the feed stream.

6. The process of claim 1 wherein said oligomerization occurs predominantly in the liquid phase.

7. The process of claim 1 wherein the density of the effluent stream is less than the density of the feed stream.

8. The process of claim 1 wherein the reactor vessel includes more than one fixed catalyst bed.

9. The process of claim 1 wherein the lighter aliphatic olefins include butenes.

10. The process of claim 1 wherein the paraffins in the saturate stream have a carbon number of at least 6.

11. The process of claim 1 wherein said product higher aliphatic olefins include octenes.

12. The process of claim 1 wherein an inert material is disposed in the reactor vessel between the fixed bed of catalyst and a reactor feed inlet.

13. The process of claim 1 wherein said product higher aliphatic olefins comprise dimerized or trimerized lighter aliphatic olefins.

14. The process of claim 1 wherein said catalyst comprises a solid phosphoric acid catalyst.

15. An oligomerization process for the production of higher aliphatic olefins, said process comprising:
   a) passing a liquid oligomerization feed comprising $C_3$ or higher aliphatic olefins to a reactor vessel;
   b) transporting said liquid oligomerization feed upwardly in said reactor vessel against gravity through a fixed bed of solid phosphoric acid catalyst under oligomerization conditions;
   c) passing a liquid saturate stream comprising $C_5$ or higher paraffins into contact with said feed stream and said catalyst; and
   d) recovering a liquid oligomerization effluent stream comprising said paraffins and $C_6$ or higher olefin product.

16. The process of claim 15 wherein said oligomerization occurs in the liquid phase.

17. The process of claim 15 wherein the density of the effluent stream is less than the density of the feed stream.

18. The process of claim 15 wherein the reactor vessel includes more than one fixed catalyst bed.

19. A process for the oligomerization of lighter aliphatic olefins to higher aliphatic olefins comprising:
   a) passing a liquid oligomerization feed stream comprising lighter aliphatic olefins to a reactor vessel, said oligomerization feed stream having a first density;
   b) transporting said liquid oligomerization feed stream upwardly in said reactor vessel against gravity through a fixed bed of solid oligomerization catalyst under oligomerization conditions, said catalyst having a Hammett acidity value of −4 or less;
   c) passing a liquid saturate stream comprising paraffins into contact with said feed stream and said catalyst; and
   d) recovering a liquid oligomerization effluent stream comprising said paraffins and product higher aliphatic olefins, said oligomerization effluent stream having a second density that is less than said first density of said oligomerization feed stream.

* * * * *